(12) United States Patent
Kamal et al.

(10) Patent No.: US 6,362,331 B1
(45) Date of Patent: Mar. 26, 2002

(54) PROCESS FOR THE PREPARATION OF ANTITUMOR AGENTS

(75) Inventors: Ahmed Kamal; Chakravarthy Laxman Nallan; Ramesh Gujjar; Ramulu Poddutoori; Srinivas Olepu, all of Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/822,782

(22) Filed: Mar. 30, 2001

(51) Int. Cl.$^7$ ............................................. C07D 519/00

(52) U.S. Cl. ....................................................... 540/497

(58) Field of Search ........................................ 540/496

(56) References Cited

FOREIGN PATENT DOCUMENTS

WO          WO 93/18045          9/1993

*Primary Examiner*—Bruck Kifle
(74) *Attorney, Agent, or Firm*—Ladas & Parry

(57) ABSTRACT

The present invention provides a process for the preparation of a novel pyrrolo[2,1-c][1,4]benzodiazepine of formula VI wherein R is H, OH, OAc and $R_1$ is H, and n is 3 to 5, by

VI

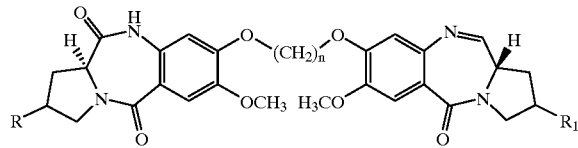

reacting (2S)-N-[4-hydroxy-5-methoxy-2-nitrobenzyl]-pyrrolidine-2-carboxy-carbaldehyde diethyl thioacetal with a dibromoalkane, isolating (2S)-N-[4-(3-bromoalkoxy)-5-methoxy-2-nitrobenzoyl]pyrrolidine-2-carboxy carbaldehyde diethyl thioacetal so formed and reacting the isolate with a dilactam, isolating 8-{[(2S)-N-5-methoxy-2-nitrobenzoyl]pyrrolidin-2-carbaldehyde diethylthioacetal}-alkoxy-7-methoxy-2,3,5,10,11,11a-hydro-1H-pyrrolo[2,1-c][1,4]benzodiazepine-5,11 dione, reducing the above nitro compound, isolating the 8-{[(2S)-N-5-methoxy-2-aminobenzoyl]pyrrolidin-2-carbaldehyde diethyl-thioacetal]-alkoxy-7-methoxy-2,3,5,10,11,11a-hydro-1H-pyrrolo[2,1-c][1,4]benzodiazepine-5,11-dione, reacting the amino compound above with a deprotecting agent to obtain the pyrrolo[2,1-c][1,4]benzodiazepines of formula VI wherein R, $R_1$ and n are as stated above.

14 Claims, No Drawings

PROCESS FOR THE PREPARATION OF ANTITUMOR AGENTS

BACKGROUND OF THE INVENTION

1. Field of the Invention

The present invention relates to a process for the preparation of antitumour agents The present invention particularly relates to a process for the preparation of novel pyrrolo[2,1-c][1,4]benzodiazepines useful as potential antitumour agents. More particularly, the present invention relates to a process for the preparation of 8-methoxy-7-(3-[7-methoxy-5-oxo(11aS)-2,3,4,11a-tetrahydro-1H-pyrrolo[2,1-c][1,4][benzodiazepine-8-yloxyalkyloxy)-(11aR)-2,3,5,10,11,11a-hexahydro-1H-pyrrolo[2,1-c][1,4]benzodiazepine-5,11-dione, with aliphatic chain length variations and their 2-hydroxy and 2-acetyloxy derivatives.

2. Description of Related Art

In the past few years, a growing interest has been shown in the development of new pyrrolo[2,1-c][1,4] benzodiazepines (PBDs). These antibiotics react covalently with DNA to form an N2-guanine adduct that lies within the minor groove of duplex DNA via an acid-labile animal bond to the electrophilic imine at the $N_{10}$–$C_{11}$ position. (Ref. Kunimoto, S., Masuda. T., Kanbayshi, N., Hamada. M., Naganawa. H., Miyamoto, M., Takeuchi, T. and Unezawa, H., *J. Antibiot.*, 1980, 33, 665; Kohn K. W. and Speous, C. L., *J. Mol. Biol.*, 1970, 51, 551.; Hurley, L. H., Gairpla, C. and Zmijewski, M., *Biocheim. Biophys Acta.*, 1977, 475, 521.; Kaplan D. J. and Hurley, L. H. *Biochmestry*, 1981, 20, 7572). The molecules have a right-handed twist allowing them to follow the curvature of the minor groove of B-form double-stranded DNA spanning three base pairs. A recent development has been the linking of two PBD units through their C-8 positions to give bisfunctional alkylating agents capable of cross-linking DNA (Ref. Thurston, D. E., Bose, D. S., Thomson, A. S., Howard, P. W., Leoni, A., Croker, S. J., Jenkins, T. C., Neidle, S. and Hurley. L. H., *J. Org. Chem.*, 1996, 61, 8141–8147).

Naturally occurring pyrrolo[2,1-c][1,4]benzodiazepines belong to a group of antitumour antibiotics derived from Streptomyces species. Recently, emphasis has been given to PBD systems as they can recognize and bind to a specific sequence of DNA. Examples of naturally occurring PBD's include anthramycin, tomaymycin, sibiromycin and neothramycin.

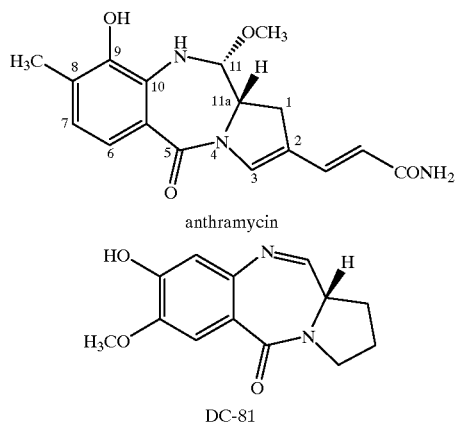

anthramycin

DC-81

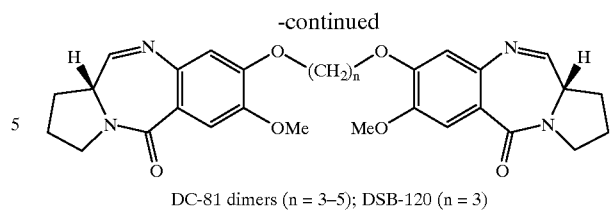

DC-81 dimers (n = 3–5); DSB-120 (n = 3)

In the last decade a number of PBD's, particularly C-8 linked PBD dimers, have been designed and synthesized to explore their effectiveness as DNA-sequence selective agents (Ref: Bose, D. S., Thomson, A. S., Ching, J. A., Hartley, J. A., Berardini. M. D., Jenkins. T. C., Neidle, S., Hurley, L. H. and Thurston. D. E., *J. Am. Chem. Soc.* 1992, 114, 4939).

Pyrrolo[2,1-c][1,4]benzodiazepine-5,11-diones are a class of compounds that bind to DNA by non-covalent interactions such as hydrophobic, Vanderwalls interactions and hydrogen bonding between ring substituents and DNA, and are also responsible for influencing sequence selectivity. Some dilactams such as (7-methoxy-2-methylcarbonyloxy-5,11-dioxo-(2S)-2,3,5,10,11,11a-hexahydro-1H-pyrrolo[2,1-c][1,4]-benzodiazepine-5,11-dione-8-yl acetate is reported to possess significant in vivo antitumour activity in P388 rat model. (Ref.: Kaneko, T., Wong, H., Doyle, T. W., Rose, W. C and Bradner. W. T., *J. Med Chem.* 1985, 28, 388)

The main object of present invention is to provide a new class of C-8 linked PBD dimers, wherein one PBD has an imine functionality while the other has an amide group. It has been envisaged that such a mixed dimer could offer more insight not only for the covalent binding but also the role played by non-covalent interactions with DNA bases.

Another object of the invention is to provide a process for the preparation of novel Pyrrolo[2,1-c][1,4]benzodiazepines useful as antitumour agents.

BRIEF SUMMARY OF THE INVENTION

Accordingly, the present invention provides a process for the preparation of a Pyrrolo[2,1-c][1,4]benzodiazepine of formula VI wherein R is H, OH, OAc; $R_1$, is H; and n is 3 to 5.

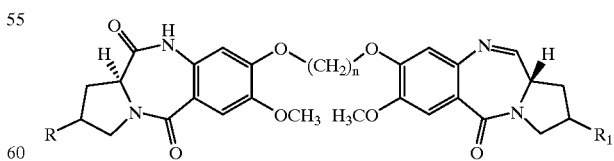

VI

The process comprises:

reacting (2S)-N-[4-hydroxy-5-methoxy-2-nitrobenzyl]-pyrrolidine-2-carboxy-carbaldehyde diethyl thioacetal of formula I wherein $R_1$ is H

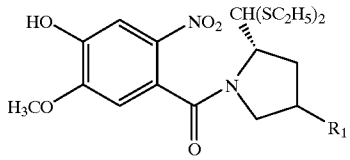

I with a dibromoalkane in an aprotic water miscible organic solvent in the presence of a mild inorganic base with a refluxing temperature for a period upto 48 hours; isolating (2S)-N [4-(3-bromoalkoxy)-5-methoxy-2-nitrobenzoyl]pyrrolidine-2-carboxy carbaldehyde diethyl thioacetal of formula II wherein $R_1$ is H;

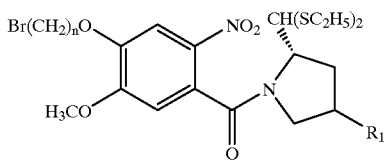

II reacting the compound of formula II with a dilactam of formula III wherein R is H, OH or OAc

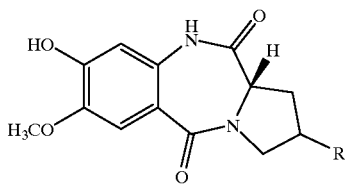

III in the presence of a mild inorganic base in the presence of an aprotic water miscible organic solvent with a refluxing temperature for a period upto 48 hours;

isolating 8-([[(2S)-N-5-methoxy-2-nitrobenzoyl] pyrrolidin-2-carbaldehyde diethylthioacetal)-alkoxy-7-methoxy-2,3,5,10,11,11a-hydro-1H-pyrrolo[2,1-c][1,4]benzodiazepine-5,11-dione of formula IV wherein R is H, OH or OAc; $R_1$ is H; and n is 3 to 5;

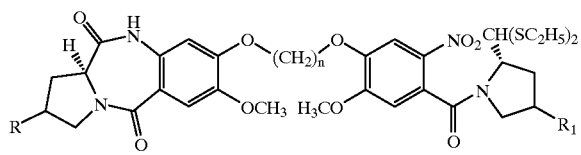

IV reducing the above nitro compound of formula IV with $SnCl_2.2H_2O$ in the presence of an organic solvent with a reflux temperature, isolating the 8-([[(2S)-N-5-methoxy-2-aminobenzoyl]pyrrolidin-2-carbaldehyde diethylthioacetal)-alkoxy-7-methoxy-2,3,5,10,11,11a-hydro-1H-pyrrolo[2,1-c][1,4]benzodiazepine-5,11-dione of formula V, wherein R is H, OH or OAc; $R_1$, is H; and n is 3 to 5; and

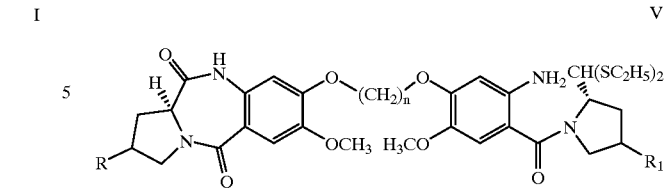

V reacting the amino compound of formula V with a deprotecting agent to obtain the pyrrolo[2,1-c][1,4] benzodiazepines of formula VI wherein R, $R_1$ and n are as stated above.

DETAILED DESCRIPTION OF THE INVENTION

In one embodiment of the invention, the aprotic water miscible organic solvent used is selected from the group consisting of acetone, tetrahydrofuran (THF) and dimethylformamide (DMF).

In another embodiment of the invention the mild inorganic base used for the reaction of compound of formula I is selected from the group consisting of $K_2CO_3$, $BaCO_3$, $Na_2CO_3$, and mixtures thereof, and the reaction is refluxed at a temperature for a period in the range of 24 to 48 hours.

In another embodiment of the invention, the compound of formula II comprises (2S)-N[4-(3-bromopropoxy)-5-methoxy-2-nitrobenzyol]pyrrolidine-2-carboxy carbaldehyde diethyl thioacetal, (2S)-N-[4-(4-bromobutoxy)-5-methoxy-2-nitrobenzoyl]pyrrolidine-2-carboxy carbaldehyde diethyl thioacetal and/or (2s)-N-[4-(5-bromopentyloxy)-5-methoxy-2-nitrobenzoyl]pyrrolidine-2-carboxy carbaldehyde diethyl thioacetal wherein $R_1$ is H.

In another embodiment of the invention, the aprotic water miscible organic solvent used when reacting the compound of formula II with the debenzylated dilactam of formula III is selected from acetone, THF and DMF. (Ref: I. Kaneko, E.: Wang, H.; Doyle T. W. *The J. Antibiotics*. 1984, 3, 300).

In yet another embodiment of the invention, the compound of formula IV comprises 8-([[(2S)-N-5-methoxy-2-nitrobenzoyl]pyrrolidin-2-carbaldehyde diethylthioacetal)-propoxy-7-methoxy-2,3,5,10,11,11a -hydro-1H-pyrrolo[2,1-c][1,4]benzodiazepine-5,11-dione, 8-([[(2S)-N-5-methoxy-2-nitrobenzoyl]pyrrolidin-2-carbaldehyde diethylthioacetal)-butoxy-7-methoxy-2,3,5,10,11,11a-hydro-1H-pyrrolo[2,1-c][1,4]benzodiazepine-5,11-dione, and/or 8-[[(2S)-N-5-methoxy-2-nitrobenzoyl]pyrrolidin-2-carbaldehyde diethylthioacetal]-pentyloxy-7-methoxy-2,3,5,10,11,11a-hydro-1H-pyrrolo[2,1,-c][1,4]benzodiazepine-5,11-dione, wherein R is H, OH or OAc and $R_1$ is H.

In another embodiment of the invention, the organic solvent used in the reduction of the nitrothioacetal compounds of the formula IV with $SnCl_2.2H_2O$ is selected from the group consisting of MeOH, DMF, 1,4-dioxane, and mixtures thereof.

In a further embodiment of the invention, the compound of formula V obtained by the reduction of compound of formula IV comprises 8-[[(2S)-N-5-methoxy-2-aminobenzoyl]pyrrolidin-2-carbaldehyde diethylthioacetal]-propoxy-7-methoxy-2,3,5,10,11,11a-hydro-1H-pyrrolo[2,1,-c][1,4]benzodiazepine-5,11-dione,8-[[(2S)-N-5-(methoxy 2-aminobenzyol]pyrrolidin-2-carbaldehyde diethylthioacetal]-butoxy-7-methoxy-2,3,5,10,11,11a-hydro-1H-pyrrolo[2,1,-c][1,4]benzodiazepine-5,11-dione, and/or 8-[[(2S)-N-5-methoxy-2-aminobenzoyl]pyrrolidin- 2-carbaldehyde diethylthioacetal]-pentyloxy-7-methoxy-2,3,5,10,11,11a-hydro-1H-pyrrolo[2,1,-c][1,4]benzodiazepine-5,11-dione, wherein R is H, OH or OAc and R₁ is H.

In another embodiment of the invention, the deprotecting agent is selected from the group consisting of HgCl₂/HgO, HgCl₂/CaCO₃ and mixtures thereof.

In another embodiment of the invention, the organic solvent used in the reduction of compound of formula V to obtain the compound of formula VI is selected from acetonitrile and MeOH.

In a further embodiment of the invention, the compound of formula IV is reduced with SnCl₂2H₂O in the presence of an organic solvent with a reflux temperature to obtain compound of formula IV comprising 8-[[(2S)-N-5-methoxy-2-aminobenzoyl]pyrrolidin-2-carbaldehyde diethylthioacetal]-propoxy-7-methoxy-2,3,5,10,11,11a-hydro-1H-pyrrolo[2,1,-c][1,4]benzodiazepine-5,11-dione, 8-[[(2S)-N-5-methoxy-2-aminobenzyol]pyrrolidin-2-carbaldehyde diethylthioacetal]-butoxy-7-methoxy-2,3,5,10,11,11a-hydro-1H-pyrrolo[2,1,-c][1,4]benzodiazepine-5,11-dione, 8-[[(2S)-N-5-methoxy-2-aminobenzoyl]pyrrolidin-2-carbaldehyde diethylthioacetal]-pentyloxy-7-methoxy-2,3,5,10,11,11a-hydro-1H-pyrrolo[2,1-c][1,4]benzodiazepine-5,11-dione, wherein R is H, OH or OAc and R₁ is H. The compound of the formula V is reacted with a deprotecting agent selected from HgCl₂/HgO and HgCl₂/CaCO₃ in the presence of an organic solvent selected from acetonitrile and MeOH, and 8-methoxy-7-3-[7-methoxy-5-oxo-(11aS)-2,3,4,11a-tetrahydro-1H-pyrrolo[2,1-c][1,4]benzodiazepine-8-yloxypropoxy-(11aR)-2,3,5,10,11,11a-hexahydro-1H-pyrrolo[2,1-c][1,4]benzodiazepine-5,11-dione, 8-methoxy-7-4[7-methoxy-5-oxo-(11aS)-2,3,4,11a-tetrahydro-1H-pyrrolo[2,1-c][1,4]benzodiazepine-8-yloxybutoxy-(11aR)-2,3,5,10,11,11a-hexahydro-1H-pyrrolo[2,1-c][1,4]benzodiazepine-5-11-dione, 8-methoxy-7-5-[7 methoxy-5-oxo-(11aS)-2,3,4,11a-tetrahydro-1H-pyrrolo[2,1-c]1,4]benzodiazepine-8-yloxypentyloxy-(11aR)-2,3,5,10,11,11a-hexahydro-1H-pyrrolo[2,1-c][1,4]benzodiazepine-5,11-dione of the formula VI wherein R, R₁ and n are as stated above, are recovered from the reaction mixture.

The precursor, (2S)-N-(4-hyxroxy-2-methoxy-2-nitrobenzoyl) pyrrolidine-2-carboxaldehyde diethyl thioacetal of formula I (intermediates of DC-81) is prepared by literature methods (Ref: Thurston, D. E.; Murthy, V. S. Langley, D. R.; Jones, G. B. Synthesis, 1990, 81).

Some representative compounds of formula VI are given below:
8-methoxy-7-3-[7-methoxy-5-oxo-(11aS)-2,3,4,11a-tetrahydro-1H-pyrrolo [2,1-c][1,4]benzodiazepine-8-yloxy]propoxy-(11aR)-2,3,5,10,11,11a-hexahydro-1H-pyrrolo[2,1-c][1,4]benzodiazepine-5,11-dione;
8-methoxy-7-3-[7-methoxy-5-oxo-(11aS)-2,3,4,11a tetrahydro-1H-pyrrolo[2,1-c][1,4]benzodiazepine-8-yloxy]butoxy-(11aR)-2,3,5,10,11,11a-hexahydro-1H-pyrrolo[2,1-c][1,4]benzodiazepine-5,11-dione;
8-methoxy-7-3-[7-methoxy-5-oxo-(11aS)-1,2,3,11a-tetrahydro-1H-pyrrolo[2,1-c][1,4]-benzodiazepine-8-yloxy]pentyloxy-(11aR)-2,3,5,10,11,11a-hexahydro-1H-pyrrolo[2,1-c][1,4]benzodiazepine-5,11 dione;
2-hydroxy-8-methoxy-7-3-[7-methoxy-5-oxo-(11aS)-2,3,5,11a-tetrahydro-1H-pyrrolo[2,1-c][1,4]benzodiazepine-8-yloxy]propoxy-(2R,11aS)-2,3,5,10,11,11a-hexahydro-1H-pyrrolo[2,1-c[1,4]benzodiazepine-5,11-dione;
2-hydroxy-8-methoxy-7-5-[7-methoxy-5-oxo(11aS)-2,3,5,11a-tetrahydro-1H-pyrrolo[2,1-c][1,4]benzodiazepine-8-yloxy]butoxy-(2R,11aS)-2,3,5,10,11,11a-hexahydro-1H-pyrrolo[2,1-c][1,4]benzodiazepine-5,11-dione;
2-hydroxy-8 methoxy-7-5-[7-methoxy-5-oxo(11aS)-2,3,5,11a-tetrahydro-1H-pyrrolo[2,1-c][1,4]benzodiazepine-8-yloxy]pentryloxy (2R,11aS)-2,3,5,10,11,11a-hexahydro-1H-pyrrolo[2,1-c][1,4]benzodiazepine-5,11-dione;
8-methoxy-7-3[7-methoxy-5-oxo-(11aS)-2,3,5,11a-tetrahydro-1H-pyrrolo[2,1-c][1,4]benzodiazepine-pine-8-yloxy]propoxy)-5,11-dioxo-(2R,11aR)-2,3,5,10,11,11a-hexahydro-1H-pyrrolo[2,1-c][1,4]benzodiazepine-2-yl acetate;
8-methoxy-7-4-[7-methoxy-5-oxo-(11aS)-2,3,5,11a-tetrahydro-1H-pyrrolo[2,1-c][1,4]benzodiazepine-8-yloxy]butoxy)-5,11-diozo-(2R,11aR)-2,3,5,10,11,11a-hexahydro-1H-pyrrolo[2,1-c][1,4]benzodiazepine-2-yl acetate; and
8-methoxy-7-(5-(7-methoxy-5-oxo-(11aS)-2,3,5,11a-tetrahydro-1H-pyrrolo[2,1-c][1,4]benzodiazepine-8-yloxy)pentyloxy)-5,11-dioxo-(2R,11aR)-2,3,5,10,11,11a-hexahydro-1H-pyrrolo[2,1-c][1,4]benzodiazepine-2-yl acetate.

The molecules synthesized are of immense biological significance with potential sequence selective DNA-binding property. This [resulted] results in design and synthesis of new congeners as illustrated in Scheme-1, having:
1. Ether linkage at C-8 position of DC-81 intermediates with dilactams.
2. Refluxing the reaction mixture for 24–48 h.
3. Synthesis of C-8 linked PBD antitumour antibiotic imines.
4. Purification by column chromatography using different solvents like ethylacetate, hexane, dichloromethane and methanol.

The reaction mechanism for the preparation of the product of the invention is given below:

Scheme-1

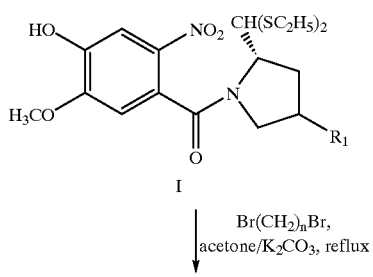

I

Br(CH₂)ₙBr,
acetone/K₂CO₃, reflux

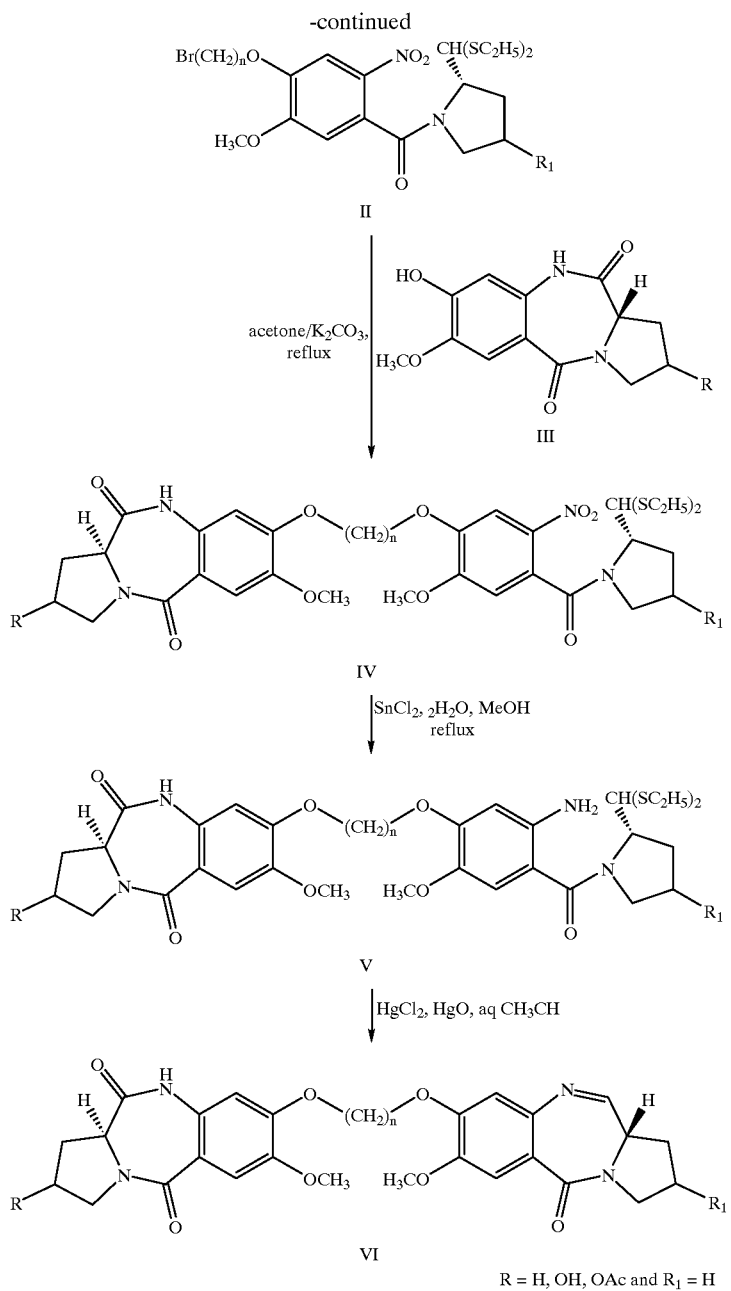

R = H, OH, OAc and R₁ = H

The following examples are given by way of illustrations and therefore should not be construed to limit the scope of the present invention.

EXAMPLE 1

A solution of (2S)-N-(4-hydroxy-5-methoxy-2 nitrobenzoyl)pyrrolidine-2-carbaldehyde diethyl thioacetal of formula I (400 mg, 1 mmol), 1,3-dibromopropane (505 mg, 2.5 mmol) and $K_2CO_3$ (414 mg, 3 mmol) in dry acetone (20 ml) was refluxed for 48 h. After the completion of reaction as indicated by TLC, EtOAc:hexane (7:3), the reaction mixture was poured on water anal then extracted with ethylacetate. Evaporation of the organic layer gave the crude product, which was further purified by column chromatography on silica gel eluting with EtOAc:hexane (1:1) to yield the pure (2S)-N-[4-(3-bromopropoxy)-5-methoxy-2-nitrobenzoyl]pyrrolidine-2-carboxy carbaldehyde diethylthioacetal of formula II.

$^1$HNMR: ($CDCl_3$) δ1.3–1.4 (m, 6H), 1.7–2.2 (m, 4H), 2.23–2.5 (m, 2H), 2.6–2.9 (m, 4H), 3.15–3.33 (m, 2H), 3.6 (t, 2H), 3.95 (s, 3H), 4.25 (t, 2H), 4.62–4.78 (m, 1H), 4.85 (d, 1H), 6.82 (s, 1H), 7.75 (s, 1H)[.]

A solution of (2S)-N-[4[(3-bromopropoxy)-5-methoxy-2-nitrobenzoyl]pyrrolidine-2-carboxy carbaldehyde diethylthioacetal of formula II (520 mg, 1 mmol), 8-hydroxy-7-methoxy-(11aS)-2,3,5,10,11,11a-hexahydro-1H-pyrrolo[2,1-c][1,4]benzodiazepine-5,11-dione (262 mg, 1 mmol) of formula III and $K_2CO_3$ (414 mg, 3 mmol) in dry acetone (20 ml) was refluxed for 48 h. After completion of reaction as indicated by TLC, EtOAc, the reaction mixture was poured on water and then extracted with ethylacetate. Evaporation of the organic layer gave the crude product, which was further purified by column chromatography on silica gel eluting with EtOAc:hexane (8:2) to obtain pure 8-([(2S)-N-5-methoxy-2-nitrobenzoyl]pyrrolidine 2-carbaldehyde diethylthioacetal)-propoxy-7-methoxy-2,3,5,10,11,11a-hexahydro-1H-pyrrolo[2,1-c][1,4]benzodiazepine-5,11-dione, of formula IV.

$^1$HNMR (CDCl$_3$) δ1.2–1.5 (m, 6H), 1.7–2.25 (m, 8H), 2.23–2.5 (m, 2H), 2.6–2.9 (m, 4H), 3.2–3.3 (m, 4H), 3.6–3.8 (m, 2H), 3.8–4.0 (s, 6H), 4.01 (m, 1H), 4.2–4.35 (m, 2H), 4.65 (m, 1H), 4.85 (d, 1H), 6.5 (s, 1H), 7.38, (s, 1H), 7,7 (s, 1H), 8.21 (s, 1H, NH exchangeable); FAB MS 703 (M1H)$^+$ The 8-([(2S)-N-5-methoxy-2-nitrobenzoyl]pyrrolidine 2-carbaldehyde diethyl thioacetal)-propoxy-7-methoxy-2,3,5,10,11,11a-hexahydro-1H-pyrrolo[2,1-c][1,4]bepzodiazepine-5,11-dione of formula IV (702 mg, 1.0 mmol) was dissolved in dichloromethane (5 mL), and methanol (10 mL). SnCl$_2$2H$_2$O (1.124 g, 5.0 mmol) was added and the mixture refluxed for 1.5 h. The reaction mixture was then carefully adjusted to a pH of 8 with saturated NaHCO$_3$ solution and then extracted with ethyl acetate (3×20 mL). The combined organic phase was dried over Na$_2$SO$_4$ and evaporated under vacuum to obtain crude 8-([(2S)-N-5-methoxy-2-aminobenzoyl]pyrrolidine 2-carbaldehyde diethylthioacetal)-propoxy-7 methoxy-2,3,5,10,11,11a-hexahydro-1H-pyrrolo[2,1-c][1,4] benzodiazepine-5,11-dione of formula V. A solution of the 8-([(2S)-N-5-methoxy-2aminobenzoyl]pyrrolidine 2-carbaldehyde diethyl thioacetal)-propoxy-7-methoxy-2,3,5,10,11,11a-hexahydro-1H-pyrrolo[2,1-c][1,4] benzodiazepine-5,11-dione of formula V (672 mg, 1 mmol), HgCl$_2$ (794 mg, 2.93 mmol) and HgO (687 mg, 3.18 mmol) in CH$_3$CN/H$_2$O (3:1 m, 15 ml) was stirred at room temperature for 12 h until TLC (EtOAc), indicated complete loss of starting material. The organic layer was then evaporated in a vacuum and the residues were diluted with EtOAc. To this, saturated NaHCO$_3$ was added slowly at room temperature and the mixture filtered through celite and washed with ethylacetate. The filtrate was evaporated in vacuum to yield crude 8-methoxy-7-3-[7-methoxy-5-oxo-(11aS)-2,3,11a-tetrahydro-1H-pyrrolo[2,1-c][1,4]-benzodiazepine-8-yloxypropoxy-(11aR)-2,3,5,10,11a-hexahydro-1H-pyrrolo[2,1-c][1,4]benzodiazepine-5,11-dione of formula VI, which was further purified by column chromatography on silica gel eluting first with ethylacetate to remove traces of mercuric salts and further eluted with methanol: CHCl$_3$ (2:8).

$^1$HNMR (DMSO-d6+CDCl$_3$) δ1.89–2.5 (m, 1OH), 3.4–4.05 (m, 13H), 4.1–4.4 (m, 3H), 6.6 (s, 1H), 6.82 (s, 1H), 7.4 (s, 1H), 7.5 (s, 1H), 7.65 (d, 1H), 9.9 (s, 1H, NH exchangeable) FAB MS-549 (M+M)$^+$

EXAMPLE 2

A solution of (2S)-N-(4-hydroxy-5-methoxy-2-nitrobenzoyl)pyrrolidine-2-carbaldehyde diethyl thioacetal of formula I (400 mg, 1 mmol), 1,3-dibromobutane (540 mg, 2.5 mmol) and K$_2$CO$_3$ (414 mg, 3 mmol) in dry acetone (20 ml) was refluxed for 48 h. After the completion of reaction as indicated by TLC, EtOAc:hexane (7:3), the reaction mixture was poured on water and then extracted with ethylacetate. Evaporation of the organic layer yielded the crude product, which was further purified by column chromatography on silica gel eluting with EtOAc:hexane (1:1) to obtain the pure (2S)-N-[4-(bromobutoxy)-5-methoxy-2-nitrobenzoyl]pyrrolidine-2-carboxy carbaldehyde diethylthioacetal of formula II.

$^1$HNMR:(CDCl$_3$) δ1.3–1.4 (m, 6H), 1.7–2.2 (m, 4H), 2.23–2.5 (m, 4H), 2.6–2.9 (m, 4H), 3.15–3.33 (m, 2H), 3.6 (t, 2H), 3.95 (s, 3H), 4.25 (t, 2H), 4.62–4.78 (m, 1H), 4.85 (d, 1H), 6.82 (s, 1H), 7.75 (s, 1H)[.]

A solution of (2S)-N-[4[(4-bromobutoxy)-5-methoxy-2-nitrobenzoyl]pyrrolidine-2-carboxy carbaldehyde diethylthioacetal of formula II (534 mg, 1 mmol), 8-hydroxy-7-methoxy-(11aS)-2,3,5,10,11,11a-hexahydro-1H-pyrrolo[2,1-c][1,4]benzodiazepine-5,11-dione (262 mg, 1 mmol) of formula III and K$_2$CO$_3$ (414 mg, 3 mmol) in dry acetone (20 ml) was refluxed for 48 h. After completion of reaction as indicated by TLC, EtOAc, the reaction mixture was poured on water and then extracted with ethylacetate. Evaporation of the organic layer gave the crude product, which was further purified by column chromatography on silica gel eluting with EtOAc:hexane (8:2) to obtain pure 8-([(2S)-N-5-methoxy-2-nitrobenzoyl]pyrrolidine 2-carbaldehyde diethylthioacetal)-butoxy-7-methoxy-2,3,5,10,11,11a-hexahydro-1H-pyrrolo[2,1-c][1,4]benzodiazepine-5,11-dione, of formula IV.

$^1$HNMR (CDCl$_3$) δ1.2–1.5 (m, 6H), 1.7–2.25 (m, 8H), 2.23–2.5 (m, 4H), 2.6–2.9 (m, 4H), 3.2–3.3 (m, 4H), 3.6–3.8 (m, 2H), 3.8–4.0 (s, 6H), 4.01 (m, 1H), 4.2–4.35 (m, 2H), 4.65 (m, 1H), 4.85 (d, IH), 6.5 (s, 1H), 7.38, (s, 1H), 7.7 (s, 1H), 8.21 (s, 1H, NH exchangeable)

The 8-([(2S)-N-5-methoxy-2-nitrobenzoyl]pyrrolidine 2-carbaldehyde diethyl thioacetal)-butoxy-7-methoxy-2,3,5,10,11,11a-hexahydro-1H-pyrrolo[2,1-c][1,4] benzodiazepine-5,11-dione of formula IV (716 mg, 10 mmol) was dissolved in dichloromethane (5 mL), and methanol (10 mL). SnCl$_2$2H$_3$O (1.124 g, 5.0 mmol) was added and the mixture and refluxed for 1.5 h. The reaction mixture was then carefully adjusted to a pH of 8 with saturated NaHCO$_3$ solution and then extracted with ethyl acetate (3×20 mL). The combined organic phase was dried over Na$_2$SO$_4$ and evaporated under a vacuum to obtain crude 8-([(2S)-N-5-methoxy-2-aminobenzoyl]pyrrolidine 2-carbaldehyde diethyl thioacetal)-butoxy-7-methoxy-2,3,5,10,11,11a-hexahydro-1H-pyrrolo[2,1-c][1,4]benzodiazepine-5,11-dione of formula V. A solution of the 8-([(2S)-N-5-methoxy-2-aminobenzoyl]pyrrolidine 2-carbaldehyde diethylthioacetal)-butoxy-7-methoxy-2,3,5,10,11,11a-hexahydro-1H-pyrrolo[2,1-c][1,4]benzodiazepine-5,11-dione of formula V (686 mg, 1 mmol), HgCl$_2$ (794 mg, 2.93 mmol) and HgO (687 mg, 3.18 mmol) in CH$_3$CN/H$_2$O (3.1 m, 15 ml) was stirred at room temperature for 12 h until TLC (EtOAc), indicates complete loss of starting material. The organic layer was then evaporated in a vacuum and the residues diluted with EtOAc. To this, saturated NaHCO$_3$ was added slowly at room temperature and the mixture filtered through celite and washed with ethylacetate. The filtrate was evaporated in a vacuum to obtain crude 8-methoxy-7(3-[7-methoxy-5-oxo-(11aS)-2,3,4,11a-tetrahydro-I H-pyrrolo[2,1-c][1,4]benzodiazepine-8-yloxybutoxy)-(11aR)-2,3,5,10,11,11a-hexahydro-1H-pyrrolo[2,1-c][1,4]benzodiazepine-5,11-dione of formula VI, which was further purified by column chromatography on silica gel eluting first with ethylacetate to remove traces of mercuric salts and further eluted with methanol: CHCl$_3$ (2:8).

$^1$HNMR (DMSO-d6+CDCl$_3$) δ1.89–2.5 (m, 12H), 3.4–4.05 (m, 13H), 4.1–4.4 (m, 3H), 6.6 (s, 1H), 6.82 (s, 1H), 7.4 (s, 1H), 7.5 (s, 1H), 7.65 (d, 1H), 9.9 (s, 1H, NH exchangeable)

EXAMPLE 3

A solution of (2S) N-(4-hydroxy-5-methoxy-2-nitrobenzoyl)pyrrolidine-2-carbaldehyde diethyl thioacetal of formula I (400 mg, 1 mmol), 1,5-dibromopentane (575 mg, 2.5 mmol) and $K_2CO_3$ (414 mg, 3 mmol) in dry acetone (20 ml) was refluxed for 48 h. After the completion of reaction as indicated by TLC, EtOAc:hexane (7:3), and the reaction mixture was poured on water and then extracted with ethylacetate. Evaporation of the organic layer gave the crude product, which was further purified by column chromatography on silica gel eluting with EtOAc:hexane (1:1) to yield the pure (2S)-N-[4-(5-bromopentyloxy)-5-methoxy-2-nitrobenzoyl]pyrrolidine-2-carboxy carbaldehyde diethylthioacetal of formula II.

$^1$HNMR ($CDCl_3$) δ1.3–1.4 (m, 6H), 1.7–2.2 (m. 4H), 2.23–2.5 (m, 6H), 2.6–2.9 (m, 4H), 3.15–3.33 (m, 2H), 3.6 (t, 2H), 3.95 (s, 3H), 4.25 (t, 2H), 4.62–4.78 (m, 1H), 4.85 (d, 1H), 6.82 (s, 1H), 7.75 (s, 1H)

A solution of (2S)-N-[4-(5-bromopentyloxy)-5-methoxy-2-nitrobezoyl]pyrrolidine-2-carboxy carbaldehyde diethylthioacetal of formula II (548 mg, 1 mmol), 8-hydroxy-7-methoxy-(11aS)-2,3,5,10,11,11a-hexahydro-1H-pyrrolo[2,1-c][1,4]benzodiazepine-5,11-dione (262 mg, 1 mmol) of formula III and $K_2CO_3$ (414 mg, 3 mmol) in dry acetone (20 ml) was refluxed for 48 h. After completion of reaction as indicated by TLC, EtOAc and the reaction mixture was poured on water and then extracted with ethylacetate. Evaporation of the organic layer gave the crude product, which was further purified by column chromatography on silica gel eluting with EtOAc,hexane (8:2) to obtain pure 8-([(2S)-N-5-methoxy-2-nitrobenzoyl]pyrrolidine 2-carbaldehyde diethylthioacetal)-pentyloxy-7-methoxy-2,3,5,10,11,11a-hexahydro-1H-pyrrolo[2,1-c][1,4] benzodiazepine-5,11-dione, of formula IV.

$^1$HNMR ($CDCl_3$) δ1.2–1.5 (m, 6H), 1.7–2.25 (m, 8H), 2.23 2.5 (m, 6H), 2.6–2.9 (m, 4H), 3.2–3.3 (m, 4H), 3.6–3.8 (m, 2H), 3.8–4.0 (s, 6H), 4.01 (m, 1H), 4.2–4.35 (m, 2H), 4.65 (m, 1H), 4.85 (d, 1H), 6.5 (s, IH), 7.38, (s, 1H), 7.7 (s, 1H), 8.21 (s,1, NH exchangeable)

The 8-([(2S)-N-5-methoxy-2-nitrobenzoyl]pyrrolidine 2-carbaldehyde diethyl thioacetal)-pentyloxy-7-methoxy-2, 3,5,10,11,11a-hexahydro-1H-pyrrolo[2,1-c][1,4] benzodiazepine-5,11-dione of formula IV (730 mg, 1.0 mmol) was dissolved in dichloromethane (5 mL), and methanol (10 mL). $SuCl_2 2H_2O$ (1.124 g, 5.0 mmol) was added and the mixture was refluxed for 1.5 h. The reaction mixture was then carefully adjusted to a pH of 8 with saturated $NaHCO_3$ solution and then extracted with ethyl acetate (3×20 mL). The combined organic phase was dried over $Na_2SO_4$ and evaporated under a vacuum to obtain crude 8-([(2S)-N-5-methoxy-2-aminobenzoyl]pyrrolidine 2-carbaldehyde diethyl thioacetal)-pentyloxy-7-methoxy-2, 3,5,10,11,11a-hexahydro-1H-pyrrolo[2,1-c][1,4] benzodiazepine-5,11-dione of formula V.

A solution of the 8-([(2S)-N 5-methoxy-2-aminobenzoyl] pyrrolidine 2-carbaldehyde diethylthioacetal)-pentyloxy-7-methoxy-2,3,5,10,11,11a-hexahydro-1H-pyrrolo[2,1-c][1,4] benzodiazepine-5,11-dione of formula V (700 mg, 1 mmol), $HgCl_2$ (794 mg, 2.93 mmol) and HgO (687mg 3.18 mmol) in $CH_3CN/H_2O$ (3:1 m, 15 ml) was stirred at room temperature for 12 h until TLC (EtOAc), indicated complete loss of starting material. Then the organic layer was evaporated in a vacuum and the residues diluted with EtOAc. To this, saturated $NaHCO_3$ was added slowly at room temperature and the mixture filtered through celite and washed with ethylacetate. The filtrate was evaporated in vacuum to obtain crude 8-methoxy-7-3-[7-methoxy-5-oxo-(11aS)-2,3,4,11a-tetrahydro-1H-pyrrolo[2,1-c][1,4]-benzodiazepine-8-yloxy] pentyloxy-(11aR)-2,3,5,10,11a hexahydro-1H -pyrrolo[2,1-c][1,4]benzodiazepine-5,11-dione of formula VI, which was further purified by column chromatography on silica gel eluting first with ethylacetate to remove traces of mercuric salts and further eluted with methanol: $CHCl_3$ (2:8).

$^1$HNMR (DMSO-d6+$CDCl_3$) δ1.89–2.5 (m, 14H), 3.4–4.05 (m,13H), 4.1–4.4 (m, 3H), 6.6 (s, 1H), 6.82 (s, 1H), 7.4 (s, 1H), 7.5 (s, 1H), 7.65 (d, 1H), 9.9 (s, 1H, NH exchangeable).

EXAMPLE 4

A solution of (2S)-N-(4-hydroxy-5-methoxy-2-nitrobenzoyl)pyrrolidine-2-carbaldehyde diethyl thioacetal of formula I (400 mg 1 mmol), 1.3-dibromopropane (505 mg, 2.5 mmol) and $K_2CO_3$ (414 mg, 3 mmol) in dry acetone (20 ml) was refluxed for 48 h. After the completion of the reaction as indicated by TLC, EtOAc:hexane (7:3), the reaction mixture was poured on water and then extracted with ethylacetate. Evaporation of the organic layer gave the crude product, which was further purified by column chromatography on silica gel eluting with EtOAc:hexane (1:1) to yield the pure (2S)-N-[4 -(3-bromopropoxy)-5-methoxy-2-nitrobenzoyl]pyrrolidine-2-carboxy carbaldehyde diethylthioacetal of formula II.

$^1$HNMR ($CDCl_3$) δ1.2–1.5 (m, 6H), 1.7–2.25 (m, 8H), 2.23 2.5 (m, 6H), 2.6–2.9 (m, 4H), 3.2–3.3 (m, 4H), 3.6–3.8 (m, 2H), 3.8–4.0 (s, 6H), 4.01 (m, 1H), 4.2–4.35 (m, 2H), 4.65 (m, 1H), 4.85 (d, 1H), 6.5 (s, IH), 7.38, (s, 1H), 7.7 (s, 1H), 8.21 (s,1, NH exchangeable).

A solution of (2S)-N-[4[(3-bromopropoxy)-5-methoxy-2-nitrobenzoyl]pyrrolidine-2-carboxy carbaldehyde diethylthioacetal of formula II (520 mg, 1 mmol), 2,8-dihydroxy-7-methoxy (2R,11aR)-2,3,5,10,11,11a-hexahydro-1H-pyrrolo [2,1-c][1,4]benzodiazepine-5,11-dione (278 mg, 1 mmol) of formula III and $K_2CO_3$ (414 mg, 3 mmol) in dry acetone (20 ml) was refluxed for 48 h. After completion of the reaction as indicated by TLC, EtOAc, the reaction mixture was poured on water and then extracted with ethylacetate. Evaporation of the organic layer gave the crude product, which was further purified by column chromatography on silica gel eluting with EtOAc;hexane (8:2) to obtain pure 8-([(2S)-N-5-methoxy-2-nitrobenzoyl]pyrrolidine 2-carbaldehyde diethylthioacetal)-propoxy-7-methoxy-(2R, 11aR) 2,3,5,10,11,11a-hexahydro-1H-pyrrolo[2,1-c][1,4] benzodiazepine-5,11-dione, of formula IV.

The 8-([(2S)-N-5-methoxy-2 nitrobenzoyl]pyrrolidine 2-carbaldehyde diethylthioacetal)-propoxy-7-methoxy(2R, 11aR)-2,3,5,10,11,11a-hexahydro-1H pyrrolo[2,1-c][1,4] benzodiazepine-5,11-dione of formula IV (718 mg, 1.0 mmol) was dissolved in dichloromethane (5 mL), and methanol (10 mL). $SnCl_2 2H_2O$ (1.124 g, 5.0 mmol) was added and the mixture refluxed for 1.5 h. The reaction mixture was then carefully adjusted to a pH of 8 with saturated $NaHCO_3$ solution and then extracted with ethyl acetate (3×20 mL). The combined organic phase was dried over $Na_2SO_4$ and evaporated under vacuum to obtain crude 8-([(2S)-N-5-methoxy-2-aminobenzoyl]pyrrolidine 2-carbaldehyde diethylthioacetal)-propoxy-7-methoxy(2R, 11aR)-2,3,5,10,11,11a-hexahydro-1H-pyrrolo[2,1-c][1,4] benzodiazepine-5,11-dione of formula V.

A solution of the 8-([(2S)-N-5-methoxy-2-aminobenzoyl] pyrrolidine 2-carbaldehyde diethylthioacetal)-propoxy-7-methoxy(2R,11aR)-2,3,5,10,11,11a-hexahydro-1H-pyrrolo [2,1-c][1,4]benzodiazepine-5,11-dione of formula V (688 mg, 1 mmol), $HgCl_2$ (794 mg, 2.93 mmol) and HgO (687 mg, 3.18 mmol) in $CH_3CN/H_3O$ (3:1 m, 15 ml) was stirred at room temperature for 12 h until TLC (EtOAc) indicated complete loss of starting material. Then the organic layer was evaporated in a vacuum and the residues diluted with EtOAc. To this, saturated NaHCO₃ was added slowly at room temperature and the mixture filtered through celite and washed with ethylacetate. The filtrate was evaporated in a vacuum to get crude 2-hydroxy-8-methoxy 7-3-[7-methoxy-5-oxo-(11aS)-2,3,5,11a-tetrahydro-1H-pyrrolo[2,1-c][1,4]-benzodiazepine-8-yloxy]propoxy-(2R,11aS)-2,3,5,10,11a-hexahydro 1H-pyrrolo[2,1-c][1,4]benzodiazepine-5,11-dione of formula VI, which was further purified by column chromatography on silica gel eluting first with ethylacetate to remove traces of mercuric salts and further eluted with methanol: CHCl₃ (2:8).

EXAMPLE 5

A solution of (2S)-N-(4-hydroxy-5-methoxy-2-nitrobenzoyl)pyrrolidine-2-carbaldehyde diethylthioacetal of formula I (400 mg, 1 mmol), 1,4-dibromobutane (540 mg, 2.5 mmol) and K₂CO₃ (414 mg, 3 mmol) in dry acetone (20 ml) was refluxed for 48 h. After the completion of the reaction as indicated by TLC, EtOAc:hexane (7:3), the reaction mixture was poured on water and then extracted with ethylacetate. Evaporation of the organic layer gave the crude product, which was further purified by column chromatography on silica gel eluting with EtOAc:hexane (1:1) to yield the pure (2S)-N-[4-(4-bromobutoxy)-5-methoxy-2-nitrobenzoyl]pyrrolidine-2-carboxy carbaldehyde diethylthioacetal of formula II.

$^1$HNMR: (CDCl₃) δ1.3 1.4 (m, 6H), 1.7–2.2 (m, 4H), 2.23–2.5 (m, 4H), 2.6–2.9 (m, 4H), 3.15–3.33 (m, 2H), 3.6 (t, 2H), 3.95 (s, 3H), 4.25 (t, 2H), 4.62–4.78 (m, 1H), 4.85 (d, 1H), 6.82 (s, 1H), 7.75 (s, 1H)

A solution of (2S)-N-[4-(3 bromobutoxy)-5-methoxy-2-nitrobenzoyl]pyrrolidine-2-carboxy carbaldehyde diethylthioacetal of formula II (534 mg, 1 mmol), 2,8-dihydroxy 7-methoxy-(2R,11aR)-2,3,5,10,11,11a-hexahydro-1H-pyrrolo[2,1-c][1,4]benzodiazepine-5,11-dione (278 mg, 1 mmol) of formula III and K₂CO₃ (414 mg, 3mmol) in dry acetone (20 ml) was refluxed for 48 h. After completion of reaction as indicated by TLC, EtOAc the reaction mixture was poured on water and then extracted with ethylacetate. Evaporation of the organic layer gave the crude product, which was further purified by column chromatography on silica gel eluting with EtOAc:hexane (9:1) to obtain pure 8-([(2S)-N-5-methoxy-2-nitrobenzoyl]pyrrolidine 2-carbaldehyde diethylthioacetal)-butoxy-2-hydroxy-7-methoxy-(2R,11aR) 2,3,5,10,11,11a-hexahydro-1H pyrrolo[2,1-c][1,4]benzodiazepine-5,11-dione, of formula IV.

The 8-([(2S)-N-5-methoxy-2-nitrobenzoyl]pyrrolidine 2-carbaldehyde diethylthioacetal)-butoxy-2-hydroxy-7-methoxy(2R,11aR)-2-3,5,10,11,11a-hexahydro-1H-pyrrolo[2,1-c][1,4]benzodiazepine-5,11-dione of formula IV (732 mg 1.0 mmol) was dissolved in dichloromethane (5 mL), and methanol (10 mL). SnCl₂2H₂O (1.124 g, 5.0 mmol) was added and the mixture refluxed for 1.5 h. The reaction mixture was then carefully adjusted to a pH of 8 with saturated NaHCO₃ solution and then extracted with ethyl acetate (3×20 mL). The combined organic phase was dried over Na₂SO₄ and evaporated under a vacuum to obtain crude 8-([(2S)-N-5-methoxy-2-aminobenzoyl]pyrrolidine 2-carbaldehyde diethylthioacetal)-butoxy-2 hydroxy-7-methoxy(2R,11aR)-2,3,5,10,11,11a-hexahydro-1H-pyrrolo[2,1-c][1,4]benzodiazepine-5,11-dione of formula V.

A solution of the 8-([(2S)-N-5-methoxy-2-aminobenzoyl] pyrrolidine 2-carbaldehyde diethylthioacetal)-butoxy-2-hydroxy-7-methoxy(2R,11aR)-2,3,5,10,11,11a-hexahydro-1H-pyrrolo[2,1-c][1,4]benzodiazepine-5,11-dione of formula V (702 mg, 1 mmol), HgCl₂ (794 mg, 2.93 mmol) and HgO (687 mg, 3.18 mmol) in CH₃CN/H₂O (3:1 m, 15 ml) was stirred at room temperature for 12 h until TLC (EtOAc), indicated complete loss of starting material. Then, the organic layer was evaporated in a vacuum and the residues diluted with EtOAc. To this, saturated NaHCO₃ was added slowly at room temperature and the mixtures filtered through celite and washed with ethylacetate. The filtrate was evaporated in a vacuum to get crude 2-hydroxy-8-methoxy-7-4-[7-methoxy-5 oxo-(11aS)-2,3,5,11a-tetrahydro-1H-pyrrolo[2,1-c][1,4]-benzodiazepine-8-yloxy]butyloxy-(2R,11aS)-2,3,5,10,11a-hexahydro-1H-pyrrolo[2,1-c][1,4]benzodiazepine-5,11-dione of formula VI, which was further purified by column chromatography on silica gel eluting first with ethylacetate to remove traces of mercuric salts and further eluted with methanol:CHCl₃ (2:8).

EXAMPLE 6

A solution of (2S) N-(4-hydroxy-5-methoxy-2-nitrobenzoyl)pyrrolidine-2-carbaldehyde diethylthioacetal of formula I (400 mg, 1 mmol), 1,5-dibromopentane (575 mg, 2.5 mmol) and K₂CO₃ (414 mg, 3 mmol) in dry acetone (20 ml) was refluxed for 48 h. After completion of the reaction as indicated by TLC, EtOAc:hexane (7:3), the reaction mixture was poured on water and then extracted with ethylacetate. Evaporation of the organic layer gave the crude product, which was further purified by column chromatography on silica gel eluting with EtOAc:hexane (1:1) to yield the pure (2S)-N-[4-(5-bromopentyloxy)-5-methoxy-2-nitrobenzoyl]pyrrolidine-2-carboxy carbaldehyde diethylthioacetal of formula II.

$^1$HNMR: (CDCl₃) δ1.3–1.4 (m, 6H), 1.7–2.2 (m, 4H), 2.23–2.5 (m, 6H), 2.6–2.9 (m, 4H), 3.15–3.33 (m, 2H), 3.6 (t, 2H), 3.95 (s, 3H), 4.25 (t, 2H), 4.62–4.78 (m, 1H), 4.85 (d, 1H), 6.82 (s, 1H), 7.75 (s, 1H)

A solution of (2S)-N-[4-(5-bromopentyloxy)-5-methoxy-2-nitrobenzoyl]pyrrolidine-2-carboxy carbaldehyde diethylthioacetal of formula II (548 mg, 1 mmol), 2,8-dihydroxy-7-methoxy-(2R,11aR)-2,3,5,10,11,11a-hexahydro-1H-pyrrolo[2,1-c][1,4]benzodiazepine-5,11-dione (278 mg, 1 mmol) of formula III and K₂CO₃ (414 mg, 3 mmol) in dry acetone (20 ml) was refluxed for 48 h. After completion of the reaction as indicated by TLC, EtOAc the reaction mixture was poured on water and then extracted with ethylacetate. Evaporation of the organic layer gave the crude product, which was further purified by column chromatography on silica gel eluting with EtOAc:hexane (9:1) to obtain pure 8-([(2S)-N-5-methoxy-2-nitrobenzoyl] pyrrolidine 2-carbaldehyde diethylthioacetal)-pentyloxy-2-hydroxy-7-methoxy-(2R,11aR)-2,3,5,10,11,11a-hexahydro-1H-pyrrolo[2,1 c][1,4]benzodiazepine-5,11-dione, of formula IV.

The 8-([(2S)-N-5-methoxy-2-nitrobenzoyl]pyrrolidine 2-carbaldehyde diethylthioacetal)-pentyloxy-2-hydroxy-7-methoxy(2R,11aR)-2,3,5,10,11,11a-hexahydro-1H-pyrrolo[2,1-c][1,4]benzodiazepine-5,11-dione of formula IV (746 mg, 1.0 mmol) was dissolved in dichloromethane (5 mL), and methanol (10 mL). SnCl₂2H₂O (1.124 g, 5.0 mmol) was added and the mixture refluxed for 1.5 h. The reaction mixture was then carefully adjusted to a pH of 8 with saturated NaHCO₃ solution and then extracted with ethyl acetate (3×20 mL). The combined organic phase was dried over Na₂SO₄ and evaporated under a vacuum to obtain crude 8-([(2S)-N-5-methoxy-2-aminobenzoyl]pyrrolidine 2-carbaldehyde diethylthioacetal)-pentyloxy-2-hydroxy-7- methoxy(2R,11aR)-2,3,5,10,11,11a-hexahydro-1H-pyrrolo[2,1-c][1,4]benzodiazepine-5,11-dione of formula V.

A solution of the 8-([(2S)-N-5-methoxy-2-aminobenzoyl]pyrrolidine 2-carbaldehyde diethylthioacetal)-pentyloxy-2-hydroxy-7-methoxy(2R,11aR)-2,3,5,10,11,11a-hexahydro-IH-pyrrolo[2,1-c][1,4]benzodiazepine-5,11-dione of formula V (716 mg, 1 mmol), $HgCl_2$ (794 mg, 2.93 mmol) and HgO (687 mg, 3.18 mmol) in $CH_3CN/H_2O$ (3:1 m, 15 ml) was stirred at room temperature for 12 h until TLC (EtOAc), indicated complete loss of starting material. Then the organic layer was evaporated in a vacuum and the residues diluted with EtOAc. To this, saturated $NaHCO_3$ was added slowly at room temperature and the mixture filtered through celite and washed with ethylacetate. The filtrate was evaporated in vacuum to obtain crude 2 hydroxy-8-methoxy-7-5[7-methoxy-5-oxo-(11aS)-2,3,5,11a-tetrahydro-1H-pyrrolo[2,1-c][1,4]-benzodiazepine-8-yloxy]pentyloxy-(2R,11aS)-2,3,5,10,11a-hexahydro-1H-pyrrolo[2,1-c][1,4]benzodiazepine-5,11-dione of formula VI, which was further purified by column chromatography on silica gel eluting first with ethylacetate to remove traces of mercuric salts and further eluted with methanol:$CHCl_3$ (2:8).

EXAMPLE 7

A solution of (2S)-N-(4-hydroxy-5-methoxy 2-nitrobenzoyl)-pyrrolidine-2-carbaldehyde diethylthioacetal of formula I (400 mg, 1 mmol), 1,3-dibromopropane (505 mg, 2.5 mmol) and $K_2CO_3$ (414 mg, 3 mmol) in dry acetone (20 ml) was refluxed for 48 h. After completion of reaction as indicated by TLC, EtOAc:hexane (7:3), reaction mixture was poured on water and then extracted with ethylacetate. Evaporation of the organic layer gave the crude product, which was further purified by column chromatography on silica gel eluting with EtOAc:hexane (1:1) to yield the pure (2S)-N-[4-(3-bromopropoxy)-5-methoxy-2-nitrobenzoyl]pyrrolidine-2-carboxy carbaldehyde diethyl thioacetal of formula II.

$^1$H NMR: ($CDCl_3$) δ1.3–1.4 (m, 6H), 1.7–2.2 (m, 4H), 2.23–2.5 (m, 2H), 2.6–2.9 (m, 4H), 3.15–3.33 (m, 2H), 3.6 (t, 2H), 3.95 (s, 3H), 4.25 (t, 2H), 4.62–4.78 (m, 1H), 4.85 (d, 1H), 6.82 (s, 1H), 7.75 (s, 1H).

A solution of (2S)-N-[4-[3 bromopropoxy)-5-methoxy-2-nitrobenzoyl]pyrrolidine-2-carboxy carbaldehyde diethylthioacetal of formula II (520 mg, 1 mmol), 8-hydroxy-7-methoxy-5,11-dioxo-(2R,11aS)-2,3,5,10,11,11a-hexahydro-1H-pyrrolo[2,1-c][1,4]benzodiazepine-2-ylacetate (320 mg, 1 mmol) of the formula III and $K_2CO_3$ (414 mg, 3 mmol) in dry acetone (20 mL) was refluxed for 48 h. After completion of the reaction as indicated by TLC, EtOAc the reaction mixture was poured on water and then extracted with ethylacetate. Evaporation of the organic layer gave the crude product, which was further purified by column chromatography on silica gel eluting with EtOAc:hexane (9:1) to yield pure 8-(3-(4-(2-di(ethylsulfanyl)methyl-(2S)-tetrahydro-1H-pyrrolylcarbonyl)-2-methoxy-5-nitrophenoxy)propoxy)-7-methoxy-5,11-dioxo-(2R,11aS)-2,3,5,10,11,11a-hexahydro-1H-pyrrolo[2,1-c][1,4]benzodiazepine-2-yl acetate of formula IV.

8-(3-(4-(2-di(ethylsulfanyl)methyl-(2S)-tetrahydro-1H-1-pyrrolycarbonyl)-2-methoxy-5-nitrophenoxy)propoxy)-7-methoxy-5,11-dioxo-(2R,11aS)-2,3,5,10,11,11a-hexahydro-1H-pyrrolo[2,1-c][1,4]benzodiazepine-2-yl acetate of formula IV (760 mg, 1.0 mmol) was dissolved in dichloromethane (5 mL), and methanol (10 mL). $SnCl_2.2H_2O$ (1,124 g, 5.0 mmol) and the reaction mixture refluxed for 1.5 h. The reaction mixture was then carefully adjusted to a pH of 8 with saturated $NaHCO_3$ solution and then extracted with ethyl acetate (3×20 mL). The combined organic phase was dried over $Na_2SO_4$ and evaporated under a vacuum to obtain the crude 8-(3-4-(2-di(ethylsulfanyl)methyl-(2 S)-tetrahydro-1H-1-pyrrolylcarbonyl)-2-methoxy-5-aminophenoxy)propoxy-7-methoxy-5,11-dioxo-(2R,11aS)-2,3,5,10,11,11a hexahydro-1H-pyrrolo[2,1-c][1,4]benzodiazepine-2-yl acetate of formula V.

A solution of the 8-(3-(4-(2-di(ethylsulfanyl)methyl-(2S)-tetrahydro-1H-1-pyrrolylcarbonyl)-2-methoxy-5-aminophenoxy)propoxy)-7-methoxy-5,11-dioxo-(2R,11aS)-2,3,5,10,11,11a-hexahydro-1H-pyrrolo[2,1-c][1,4]benzodiazepine-2-yl acetate of formula V (730 mg, 1 mmol), $HgCl_2$ (794 mg, 2.93 mmol) and HgO (687 mg, 3.18 mmol) in $CH_3CN/H_2O$ (3:1, 15 ml) was stirred at room temperature for 12 h until TLC (EtOAc), indicated complete loss of starting material. Then the organic layer was evaporated in a vacuum and the residue is diluted with EtOAc. To this, saturated $NaHCO_3$ was added slowly at room temperature and the mixture filtered through celite and washed with ethylacetate. The filtrate was evaporated in a vacuum to obtain crude 7-methoxy-8-(4-(7-methoxy-5-oxo (11aR)-2,3,5,11a-tetrahydro-1H-pyrrolo[2,1-c][1,4]benzodiazepine-8-yloxy)propoxy)-5,11-dioxo-(2R,11aS)-2,3,5,10,11,11a-hexahydro-1H-pyrrolo[2,1-c][1,4]benzodiazepine-2-yl acetate of formula VI, which was further purified by column chromatography on silica gel by eluting first with ethylacetate to remove traces of mercuric salts and then with MeOH:$CHCl_3$ (2:8).

EXAMPLE 8

A solution of (2S)-N-(4-hydroxy-5-methoxy-2-nitrobenzoyl)-pyrrolidine-2-carbaldehyde diethyl thioacetal of formula I (400 mg, 1 mmol), 1,4-dibromobutane (540 mg, 2.5 mmol) and $K_2CO_3$ (414 mg, 3 mmol) in dry acetone (20 ml) was refluxed for 48 h. After completion of the reaction as indicated by TLC, EtOAc:hexane (7:3), reaction mixture was poured on water and then extracted with ethylacetate. Evaporation of the organic layer gave the crude product, which was further purified by column chromatography on silica gel by eluting with EtOAc:hexane (1:1) to yield pure (2S)-N-[4-(4-bromobutoxy)-5-methoxy-2-nitrobenzoyl]pyrrolidine-2-carboxy carbaldehyde diethyl thioacetal of formula II.

$^1$HNMR: ($CDCl_3$) δ1.3–1.4 (m, 6H), 1.7–2.2 (m, 4H), 2.23–2.5 (m, 4H), 2.6–2.9 (m, 4H), 3.15–3.33 (m, 2H), 3.6 (t, 2H), 3.95 (s, 3H), 4.25 (t, 2H), 4.62–4.78 (m, 1H), 4.85 (d, 1H), 6.82 (s, 1H), 7.75 (s, 1H)

A solution of (2S)-N-[4-(4-bromobutoxy)-5-methoxy-2-nitrobenzoyl]pyrrolidine-2-carboxy carbaldehyde diethyl thioacetal of formula II (534 mg, 1 mmol), 8-hydroxy-7-methoxy-5,11-dioxo-(2R,11aS)-2,3,5,10,11,11a-hexahydro-1H-pyrrolo[2,1-c][1,4]benzodiazepine-2-ylacetate (320 mg, 1 mmol) of the formula III and $K_2CO_3$ (414 mg, 3 mmol) in dry acetone (20 mL) was refluxed for 48 h. After completion of the reaction as indicated by TLC, EtOAc, the reaction mixture was poured on water and then extracted with ethylacetate. Evaporation of the organic layer gave the crude product, which was further purified by column chromatography on silica gel by eluting with EtOAc:hexane (9:1) to give pure 8-(4-(4-(2-di(ethylsulfanyl)methyl-(2S)-tetrahydro-1H-pyrrolylcarbonyl)-2-methoxy-5-nitrophenoxy)butoxy)-7-methoxy-5,11-dioxo-(2R,11aS)-2,3,5,10,11,11a-hexahydro-1H-pyrrolo[2,1-c][1,4]benzodiazepine 2-yl acetate of formula IV.

8-(4-(4-(2-di(ethylsulfanyl)methyl-(2S)-tetrahydro-1H-1-pyrrolycarbonyl)-2-methoxy-5-nitrophenoxy)butoxy)-7- methoxy-5,11-dioxo-(2R,11aS)-2,3,5,10,11,11a-hexahydro-1H-pyrrolo[2,1-c][1,4]benzodiazepine-2-yl acetate of formula IV (774 mg, 1.0 mmol) was dissolved in dichloromethane (5 mL), and methanol (10 mL). $SnCl_2 2H_2O$ (1.124 g, 5.0 mmol) was added and the reaction mixture refluxed for 1.5 h. The reaction mixture was then carefully adjusted to a pH of 8 with saturated $NaHCO_3$ solution and then extracted with ethyl acetate (3×20 mL). The combined organic phase was dried over $Na_2SO_4$ and evaporated under a vacuum to obtain crude 8-(4-4-(2-di(ethylsulfanyl)methyl-(2S)-tetrahydro-1H-1-pyrrolylcarbonyl)-2-methoxy-5-aminophenoxy)butoxy-7-methoxy-5,11-dioxo-(2R,11aS)-2,3,5,10,11,11a-hexahydro-1H-pyrrolo[2,1-c][1,4]benzodiazepine-2-yl acetate of formula V.

A solution of the 8-(4-(4-(2-di(ethylsulfanyl)methyl-(2S)-tetrahydro-1H-1-pyrrolylcarbonyl)-2-methoxy-5-aminophenoxy)butoxy)-7-methoxy-5,11-dioxo-(2R,11aS)-2,3,5,10,11,11a-hexahydro-1H-pyrrolo[2,1-c][1,4]benzodiazepine-2-yl acetate of formula V (744 mg, 1 mmol), $HgCl_2$ (794 mg, 2.93 mmol) and HgO (687 mg, 3.18 mmol) in $CH_3CN/H_2O$ (3:1, 15 ml) was stirred at room temperature for 12 h until TLC (EtOAc) indicated complete loss of starting material. Then the organic layer was evaporated in a vacuum and the residue was diluted with EtOAc. To this, saturated $NaHCO_3$ was added slowly at room temperature and the mixture was filtered through celite and washed with ethylacetate. The filtrate was evaporated in a vacuum to obtain crude 7-methoxy-8-(4-(7-methoxy-5-oxo-(11aR)-2,3,5,11a-tetrahydro-1H-pyrrolo[2,1-c][1,4]benzodiazepine-8-yloxy)butoxy)-5,11-dioxo-(2R,11aS)-2,3,5,10,11,11a-hexahydro-1H-pyrrolo[2,1-c][1,4]benzodiazepine-2-yl acetate of formula VI, which was further purified by column chromatography on silica gel by eluting first with ethylacetate to remove traces of mercuric salts and then with MeOH:CHCl$_3$ (2:8).

EXAMPLE 9

A solution of (2S)-N-(4-hydroxy-5-methoxy-2-nitrobenzoyl)-pyrrolidine-2-carbaldehyde diethyl thioacetal of formula I (400 mg, 1 mmol), 1,5-dibromopentane (575 mg, 2.5 mmol) and $K_2CO_3$ (414 mg, 3 mmol) in dry acetone (20 ml) was refluxed for 48 h. After completion of the reaction as indicated by TLC, EtOAc:hexane (7:3), the reaction mixture was poured on water and then extracted with ethylacetate. Evaporation of the organic layer gave the crude product, which was further purified by column chromatography on silica gel by eluting with EtOAc:hexane (1:1) to yield pure (2S)-N-[4-(5-bromopentyloxy)-5-methoxy-2-nitrobenzoyl]pyrrolidine-2-carboxy carbaldehyde diethyl thioacetal of formula II.

$^1$HNMR: (CDCl$_3$) δ1.3–1.4 (m, 6H), 1.7–2.2 (m, 4H), 2.23–2.5 (m, 4H), 2.6–2.9 (m, 4H), 3.15–3.33 (m, 2H), 3.6 (t, 2H), 3.95 (s, 3H), 4.25 (t, 2H), 4.62–4.78 (m, 1H), 4.85 (d, 1H), 6.82 (s, 1H), 7.75 (s, 1H).

A solution of (2S)-N-[4-(5-bromopentyloxy)-5-methoxy-2-nitrobenzoyl]pyrrolidine-2-carboxy carbaldehyde dieth-yl thioacetal of formula II (548 mg, 1 mmol), 8-hydroxy-7-methoxy-5,11-dioxo-(2R,1 aS)-2,3,5,10,11,11a-hexahydro-1H-pyrrolo[2,1-c][1,4]benzodiazepine-2-ylacetate (320 mg, 1 mmol) of formula III and $K_2CO_3$ (414 mg, 3 mmol) in dry acetone (20 mL) was refluxed for 48 h. After completion of the reaction as indicated by TLC, EtOAc, the reaction mixture was poured on water and then extracted with ethylacetate. Evaporation of the organic layer gave the crude product, which was further purified by column chromatography on silica gel by eluting with EtOAc:hexane (9:1) to give pure 8-(5-(4-(2-di(ethylsulfanyl)methyl-(2S)-tetrahydro-1H-pyrrolycarbonyl)-2-methoxy-5-nitrophenoxy)pentyloxy)-7-methoxy -5,11-dioxo-(2R,11aS)-2,3,5,10,11,11a-hexahydro-1H-pyrrolo[2,1-c][1,4]benzodiazepine-2-yl acetate of formula IV.

8-(4-(5-(2-di(ethylsulfanyl)methyl-(2S)-tetrahydro-1H-1-pyrrolycarbonyl)-2-methoxy -5-nitrophenoxy)pentyloxy)-7-methoxy-5,11-dioxo-(2R,11aS)2,3,5,10,11,11a-hexahydro-1H-pyrrolo[2,1-c][1,4]benzodiazepine-2-yl acetate of formula IV (788 mg, 1.0 mmol) was dissolved in dichloromethane (5 mL), and methanol (10 mL). $SnCl_2 2H_2O$ (1.124 g, 5.0 mmol) was added to the reaction mixture and refluxed for 1.5 h. The reaction mixture was then carefully adjusted to a pH of 8 with saturated $NaHCO_3$ solution and then extracted with ethyl acetate (3×20 mL). The combined organic phase was dried over $Na_2SO_4$ and evaporated under a vacuum to obtain crude 8-(5-4-(2-di(ethylsulfanyl)methyl-(2S) tetrahydro-1H-1-pyrrolylcarbonyl)-2-methoxy-5-aminophenoxy)pentyloxy)-7-methoxy-5,11-dioxo-(2R,11aS)-2,3,5,10,11,11a-hexahydro-1H-pyrrolo[2,1-c][1,4]benzodiazepine-2-yl acetate of formula V.

A solution of the 8-(5-(4-(2-di(ethylsulfanyl)methyl-(2S)-tetrahydro-1H-1-pyrrolylcarbonyl)-2-methoxy-5-aminophenoxy)pentyloxy)-7-methoxy-5,11-dioxo-(2R,11aS)-2,3,5,10,11,11a-hexahydro-1H-pyrrolo[2,1-c][1,4]benzodiazepine-2-yl acetate of formula V (758 mg, 1 mmol), $HgCl_2$ (794 mg, 2.93 mmol) and HgO (687 mg, 3.18 mmol) in $CH_3CN/H_2O$ (3:1, 15 ml) was stirred at room temperature for 12 h until TLC (EtOAc), indicated complete loss of starting material. The organic layer was evaporated in a vacuum and the residue was diluted with EtOAc. To this, saturated $NaHCO_3$ was added slowly at room temperature and the mixture was filtered through celite and washed with ethylacetate. The filtrate was evaporated in a vacuum to obtain crude 7-methoxy-8 (4-(7-methoxy-5-oxo-(11aR)-2,3,5,11a-tetrahydro-1H-pyrrolo[2,1-c][1,4]benzodiazepine-8-yloxy)pentyloxy)-5,11-dioxo-(2R,11aS)-2,3,5,10,11,11a-hexahydro-1H-pyrrolo[2,1 -c][1,4]benzodiazepine-2-yl acetate of formula VI, which was further purified by column chromatography on silica gel by eluting first with ethylacetate to remove traces of mercuric salts and then further with MeOH:CHCl$_3$ (2:8).

Biological Activity: In vitro anticancer activity studies were carried out at National Caner Institute (USA) and the thermal denaturation of DNA was performed at School of Life Science, University of Hyderabad.

Table 1: Thermal denaturation with calf thymus DNA[a], at a [PBD]:[DNA]molar ratio of 1:5[b] and in vitro one dose primary anticancer assay[c] in the NCI-H460, MCF 7 and SF-268 for Vi, wherein R is H; R$_1$ is H, OH or OAc; and n is 3 to 5.

| Induced ΔTm/C[a,b] after | | Growth Percentage | | |
|---|---|---|---|---|
| Incubation at 37° C. for | | (Lung) | (Breast) | (CNS) |
| Compound | 0 h | 18 h | NCI-H460 | MCF 7 | SF-268 |
| VI (n is 3) | 6.5 | 7.0 | 4 | 10 | 11 |
| VI (n is 4) | 5.0 | 8.5 | −16 | −41 | −81 |
| VI (n is 5) | 14.0 | 17.0 | −39 | 7 | −21 |
| DC-81 | 0.3 | 0.7 | — | — | — |
| DSB-120 | 10.2 | 15.4 | — | — | — |

Interestingly, the data presented in Table 1 shows that as the size of the linker spacer increases from 3–5, the DNA stabilisation is also enhanced. In this assay, for a 1:5 molar ratio of (PBD):(DNA), one of this mixed imine-amide PBD dimer VI, where n is 5, elevates the helix melting temperature of CT DNA remarkably to 17° C. after incubation for 18 h at 37° C. In similar conditions, the dimer having two imino functionalities, i.e. DSB-120, provides a ΔTm of 15.4° C. On the other hand, the naturally occurring DC-81 having only one imino group exhibits a ΔTm of 0.7° C. This demonstrates that the compound VI, where n is 5 containing a single imino functionality shows a very significant DNA binding affinity. To the best of our knowledge, this is the first synthetic non-cross-linking molecule which has exhibited a remarkable DNA binding effect that is similar to the naturally occurring sibiromycin (ΔTm–16.3° C. at 18 h). This data indicates that non-covalent interactions play an important role for the enhancement of DNA binding affinity. The preliminary anticancer assay carried out in the three human cell lines: lung (NCI-H460), breast (MCF7) and CNS (SF-268) exhibit significant anticancer activity for these compounds as illustrated in Table 1.

We claim:

1. A process for the preparation of a Pyrrolo[2,1-c][1,4] benzodiazepine of formula VI wherein R is H, OH, OAc and $R_1$ is H, and n is 3 to 5,

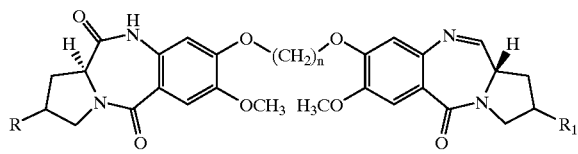

VI said process comprising reacting (2S)-N-[4-hydroxy-5-methoxy-2-nitrobenzyl]-pyrrolidine-2-carboxy-carbaldehyde diethyl thioacetal of formula I wherein $R_1$ is H

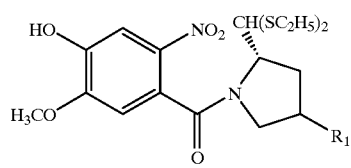

I with a dibromoalkane in a aprotic water miscible organic solvent in the presence of mild inorganic base upto refluxing temperature for a period upto 48 hours, isolating (2S)-N-[4-(3-bromoalkoxy)-5-methoxy-2-nitrobenzoyl]pyrrolidine-2-carboxy carbaldehyde diethyl thioacetal of formula II wherein $R_1$ is H,

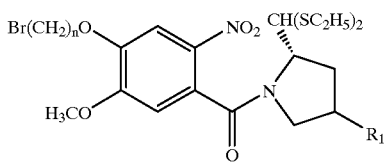

II reacting the compound of formula II with a dilactam of formula III wherein R is H, OH or OAc

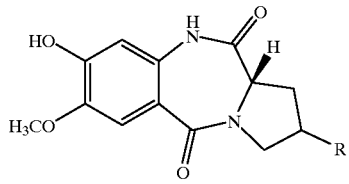

III in presence of a mild inorganic base in presence of an aprotic water miscible organic solvent upto refluxing temperature for a period upto 48 hours, isolating 8-{[(2S)-N-5-methoxy-2-nitrobenzoyl]pyrrolidin-2-carbaldehyde diethylthioacetal}-alkoxy-7-methoxy-2,3,5,10,11,11a-hydro-1H-pyrrolo[2,1-c][1,4]benzodiazepine-5,11-dione of formula IV wherein R is H, OH, or OAc and $R_1$ is H and n is 3 to 5,

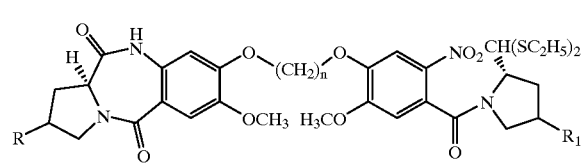

IV reducing the above nitro compound of formula IV with $SnCl_2 2H_2O$ in the presence of an organic solvent upto a reflux temperature, isolating the 8-[[(2S)-N-5-methoxy-2-aminobenzoyl]pyrrolidin-2-carbaldehyde diethylthioacetal]-alkoxy-7-methoxy-2,3,5,10,11,11a-hydro 1H-pyrrolo[2,1-c][1,4]benzodiazepine-5,11-dione of formula V, wherein R is H, OH or OAc, $R_1$ is H and n is 3 to 5,

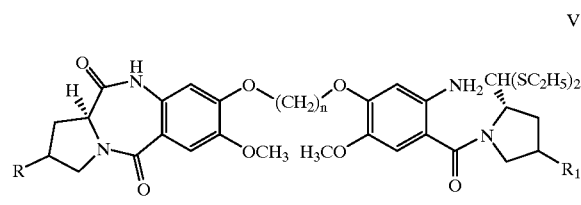

V reacting the amino compound of formula V with a deprotecting agent to obtain the pyrrolo[2,1-c][1,4] benzodiazepines of formula VI wherein R, $R_1$ and µ are as stated above.

2. A process as claimed in claimed 1 wherein the aprotic water miscible organic solvent used is selected from the group consisting of acetone, tetrahydrofuran (THF) and dimethylformamide (DMF).

3. A process as claimed in claim 1 wherein the mild inorganic base used for the reaction of compound of formula J is selected from the group consisting of $K_2CO_3$, $BaCO_3$, and $Na_2CO_3$ and the reaction is upto refluxing temperatures for a period in the range of 24 to 48 hours.

4. A process as claimed in claim 1 wherein the compound of formula II obtained comprises (2S)-N[4-(3-bromopropoxy)-5-methoxy-2-nitrobenzyol]pyrrolidine-2-carboxy carbaldehyde diethyl thioacetal, (2S)-N-[4-(4-bromobutoxy)-5-methoxy-2-nitrobenzoyl]pyrrolidine 2-carboxy carbaldehyde diethyl thioacetal and/or (2S)-N-[4-(5-bromopentyloxy)-5-methoxy-2-nitrobenzoyl]pyrrolidine-2-carboxy carbaldehyde diethyl thioacetal wherein $R_1$ is H.

5. A process as claimed in claim 1 wherein the aprotic water miscible organic solvent used when reacting compound of the formula II with the debenzylated dilactam of formula III is selected from acetone, THF and DMF.

6. A process as claimed in claim 1 wherein the compound of formula IV obtained comprises 8 {[(2S)-N-5-methoxy-2-nitrobenzoyl]pyrrolidin-2-carbaldehyde diethylthioacetal]-propoxy 7-methoxy-2,3,5,10,11,11a-hydro-1H-pyrrolo[2,1-c]1,4]benzo-diazepine-5,11-dione, 8-{[(2S)-N-5-methoxy-2-nitrobenzoyl]pyrrolidin-2-carbaldehyde diethylthioacetal]-butoxy 7-methoxy-2,3,5,10,11,11a-hydro-1H-pyrrolo[2,1-c][1,4]benzodiazepine-5,11-dione, and/or 8-{[2S)-N-5-methoxy-2-nitrobenzoyl]pyrrolidin-2-carbaldehyde diethylthioacetal]-pentyloxy-7-methoxy-2,3,5,10,11,11a-hydro-1H-pyrrolo{2,1,c][1,4]benzodiazepine-5,11-dione, wherein R is H, OH or OAc and $R_1$ is H.

7. A process as claimed in claim 1 wherein the organic solvent used in the reduction of the nitrothioacetal compounds of the formula IV with $SnCl_2.2H_2O$ is selected from the group consisting of McOH, DMF and 1,44-dioxane or any mixture thereof.

8. A process claimed in claim 1 wherein the compound of formula V obtained by the reduction of compound of formula IV comprises 8-{[(2S)-N-5-methoxy-2-aminobenzoyl]pyrrolidin-2-carbaldehyde diethylthioacetal]-propoxy-7-methoxy-2,3,5,10,11,11a-hydro-1H-pyrrolo-[2,1-c][1,4]benzodiazepine-5,11-dione, 8-{[(2S) N-5-methoxy-2-aminobenzoyl]pyrrolidin 2-carbaldehyde diethylthioacetal]-butoxy-7 -methoxy-2,3,5,10,11,11a-hydro-1H-pyrrolo[2,1,-c][1,4]benzodiazepine -5,11,-dione, and/or 8-{[(2S)-N-5-methoxy-2-aminobenzoyl]pyrrolidin-2-carbaldehyde diethylthioacetal]-pentyloxy-7-methoxy-2,3,5,10,11,11a-hydro -1H-pyrrolo[2,1-c][1,4]benzodiazepine-5,11-dione, wherein R is H, OH or OAc and $R_1$ is H.

9. A process as claimed in claim 1 wherein the deprotecting agent is selected from $HgCl_2/HgO$ and $HgCl_2/CaCO_3$.

10. A process as claimed in claim 1 wherein the organic solvent used in the reduction of compound of formula V to obtain the compound of formula VI is selected from acetonitrile and MeOH.

11. A process as claimed in claim 1 wherein the compound of formula IV is reduced with $SnCl_2.2H_2O$ in the presence of an organic solvent upto a reflux temperature to obtain compound of formula V comprising 8-{[(2S)-N-5-methoxy-2-aminobenzoyl]pyrrolidin 2-carbaldehyde diethylthioacetal]-propoxy-7-methoxy-2,3,5,10,11,11a-hydro-1H-pyrrolo-[2,10c][1,4]benzodiazepine-5,11-dione, 8-{[(2S)-N-5-methoxy-2-aminobenzoyl]pyrrolidin-2-carbaldehyde diethylthioacetal]-butoxy-7-methoxy-2,3,5,10,11,11a-hydro-1H-pyrrolo[2,1,c][1,4}benzodiazepine-5,11-dione, 8-{[(2S)-N-5-methoxy-2-aminobenzoyl]pyrrolidin-2-carbaldehyde diethylthioacetal]-pentyloxy-7-methoxy-2,3,5,10,11,11a-hydro-1H -pyrrolo[2,1-c][1,4]benzodiazepine-5,11-dione, wherein R is H, OH or OAc and $R_1$ is H.

12. A process as claimed in claim 11 wherein the compound of the formula V is reacted with a deprotecting agent selected from $HgCl_3/HgO$ and $HgCl_2/CaCO_3$ in the presence of an organic solvent selected from acrylonitrile and MeOH, and 8-methoxy-7-{3-[7-methoxy-5-oxo-(11aS)-2,3,4,11a-tetrahydro-1H -Pyrrolo[2,1-c][1,4]benzodiazepine-8-yloxypropoxy}-(11aR)-2,3,5,10,11,11a -hexahydro-1H-Pyrrolo[2,1-c][1,4]benzodiazepine 5,11-dione-8-methoxy-7-{4-[7-methoxy-5-oxo-(11aS)2,3,4,11a-tetrahydro-1H-Pyrrolo[2,1-c][1,4]benzodiazepine-8-yloxybutoxy}-(11aR)-2,3,5,10,11,11a-hexahydro -1H-Pyrrolo[2,1-c][1,4]benzodiazepine-5,11-dione, 8-methoxy-7-{5-[7-methoxy-5-oxo-(11aS)-2,3,4,11a-tetrahydro-1H-pyrrolo[2,1-c]1,4]benzodiazepine-8-yloxypentyloxy}-(11aR)-2,3,5,10,11,11a-hexahydro -1H-pyrrolo[2,1-c][1,4]benzodiazepine-5,11-dione of the formula VI wherein R, $R_1$ and n are as stated above are recovered from the reaction mixture.

13. A process as claimed in claim 1 wherein nitrodiethyl thioacetal pyrrolo[2,1-c][1,4]benzodiazepine of formula III comprises C-8 linked to dilactam without or with substitutions in the proline ring such as H or OH.

14. A process as claimed in claim 1 wherein the dibromoalkane used has 3 carbon to 5 carbons.

* * * * *